United States Patent
Walsum et al.

(10) Patent No.: US 6,506,723 B1
(45) Date of Patent: *Jan. 14, 2003

(54) SINGLE PHASE AQUEOUS SURFACTANT-FREE NONTOXIC AIR FRESHENING COMPOSITION AND WICK-CONTAINING AIR FRESHENING DEVICE USING SAID COMPOSITION

(75) Inventors: Arnoud Van Walsum, Soest (NL); Jan-Willem Zacharias Ruizendaal, Barneveld (NL); Richard M. Boden, Ocean, NJ (US); Andrew John Crossman, Amsterdam (NL); Michael John Robert White, Amsterdam (NL)

(73) Assignee: International Flavors & Fragrances Inc., New York, NY (US)

( * ) Notice: Subject to any disclaimer, the term of this patent is extended or adjusted under 35 U.S.C. 154(b) by 226 days.

This patent is subject to a terminal disclaimer.

(21) Appl. No.: 09/630,731

(22) Filed: Aug. 2, 2000

Related U.S. Application Data

(63) Continuation-in-part of application No. 09/383,969, filed on Aug. 26, 1999, now Pat. No. 6,180,595.

(51) Int. Cl.[7] .................................................. A61K 7/46
(52) U.S. Cl. ................................. 512/1; 512/3; 239/44; 424/76.4; 424/402
(58) Field of Search .......................... 512/1, 3; 424/402, 424/76.4; 239/44

(56) References Cited

U.S. PATENT DOCUMENTS

| | | | | |
|---|---|---|---|---|
| 4,601,938 A | * | 7/1986 | Deacon et al. | ........... 15/104.93 |
| 4,663,081 A | | 5/1987 | Grimshaw et al. | |
| 5,837,065 A | * | 11/1998 | Haley et al. | ................... 134/42 |
| 6,143,707 A | * | 11/2000 | Trinh et al. | ................. 134/25.2 |

FOREIGN PATENT DOCUMENTS

| | | |
|---|---|---|
| EP | 0 520 547 A2 | 12/1992 |
| EP | 0 520 547 A3 | 12/1992 |
| EP | 0 864 637 A1 | 9/1998 |
| JP | 8113522 A2 | 5/1996 |
| WO | WO 97/45516 | 12/1997 |

* cited by examiner

*Primary Examiner*—Jill Warden
*Assistant Examiner*—Monique T. Cole
(74) *Attorney, Agent, or Firm*—Arthur L. Liberman

(57) ABSTRACT

Described is a single phase aqueous surfactant-free nontoxic air freshening composition containing 30–70% water, 5–20% of a fragrance, at least 60% of the components of which has a C $\log_{10} P \leq 2.5$ and 30–60 weight percent of a mixture of two glycol ether components:

(i) dipropylene glycol methyl ether; and
(ii) propylene glycol propyl ether or propylene glycol butyl ether.

Also described is an air freshener device comprising a vessel for the aforementioned composition, an emanating surface and a wick for supplying the composition to the emanating surface. In another embodiment of the invention is a stain removal wipe, which contains a fragrant aqueous system with low solvent and substantially free of surfactant.

12 Claims, No Drawings

SINGLE PHASE AQUEOUS SURFACTANT-FREE NONTOXIC AIR FRESHENING COMPOSITION AND WICK-CONTAINING AIR FRESHENING DEVICE USING SAID COMPOSITION

STATUS OF RELATED APPLICATIONS

This application is a Continuation-in-part of U.S. Ser. No. 09/383,969, filed on Aug. 26, 1999, now U.S. Pat. No. 6,180,595 B1 issued on Jan. 30, 2001.

BACKGROUND OF THE INVENTION

Our invention relates to single phase aqueous surfactant-free nontoxic air freshening compositions and wick-containing air freshening devices using such compositions.

Conventional liquid air fresheners generally comprise a reservoir containing a mixture which may be a true solution, a colloidal solution or a microemulsion of a perfume with a solvent into which dips a wick which is connected to an emanating surface. The perfume mixture travels up the wick to the emanating surface from which the perfume evaporates and freshens the surrounding atmosphere. Perfumes used in those air fresheners are generally oils and are therefore generally insoluble in water in the absence of any other agents. Systems in which the perfume solution is aqueous based therefore always contain a surface active agent which solubilizes the perfume in water. The amount of surfactant has to be quite high, for instance, 10–15% or more by weight based on the total composition.

The surfactants used in such compositions are conventional surfactants, generally anionic surfactants such as alkyl benzene sulfonates and lauryl sulfates. Nonionic surfactants have also been used, but they are more expensive and tend to depress the perception of the perfume odor. These surface active agents are all nonvolatile, and they therefore do not evaporate from the emanating surface. The concentration of surfactant in the emanating surface therefore gradually increases, and the presence of surfactant impedes the progress of perfume in the wick and also prevents the perfume emanating as it should.

Most aqueous based systems also contain a cosolvent in addition to the perfume and surfactant. Examples of cosolvents are ethanol and diethylene glycol monoethyl ethers (DEGMEE). Such compositions always contain a surfactant and therefore suffer the same disadvantages as described above.

Some liquid air fresheners contain little or no water and so are free of surfactant. For example, a solution of perfume in DEGMEE having the structure:

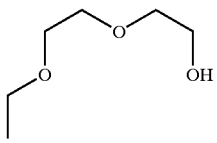

and water is stable as a single phase provided the amount of water is low, for example, below 20% when the amount of perfume is about 10% by weight. Since these compositions cannot tolerate high amounts of water, they tend to be expensive.

U.S. Pat. No. 3,945,950 (incorporated by reference herein) describes solid air freshener compositions, which suffer from different problems to the air fresheners comprising liquid compositions with which our invention is concerned. The solid compositions contain perfume, a diethylene glycol monoalkyl ether and a gelling agent, which is a surface active fatty acid soap or metal salt thereof and an inert liquid. Water is sometimes included in the compositions as some or all of the inert liquid, but only in small amounts of 4% by weight.

In U.S. Pat. No. 4,663,081 issued on May 5, 1987 (the specification for which is incorporated by reference herein), it is indicated that diethylene glycol monobutyl ether (DEGMBE) having the structure:

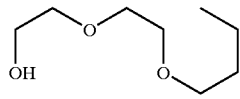

can, when containing dissolved perfume, incorporate a surprisingly large amount of water compared to other glycol ethers and is therefore more cost effective. It is further indicated in U.S. Pat. No. 4,663,081 that the mixture of DEGMBE and water also has very suitable volatility properties and has a beneficial effect on the rate of emanation of the perfume. It is further indicated in U.S. Pat. No. 4,663,081 that the composition containing the DEGMBE generally comprises between 5 and 30% by weight of perfume; usually between 8 and 20% by weight of perfume and often 10% by weight. It is further indicated in U.S. Pat. No. 4,663,081 that the amounts of perfume in compositions containing DEGMBE affect the amount of water that can be mixed into the solution before a phase separation occurs. It is stated that, for example, when the concentration of perfume in the solution is 10% by weight then the maximum amount of water that can be incorporated in a one phase solution is about 55% by weight, and for a perfume solution at 20% concentration, the maximum amount of water is about 40% by weight.

It is further indicated in U.S. Pat. No. 4,663,081 that the perfume may be any of the perfumes conventionally used in air fresheners and that "the identity of the perfume makes little difference to the behavior of the solvent system. It is further indicated in U.S. Pat. No. 4,663,081:

"Solutions of perfume in various glycol ethers of varying concentration were loaded with water until phase separation occurred. The maximum amounts of water tolerated in systems at various perfume concentrations for the glycol ethers tested is shown in Table 1.

TABLE 1

Maximum amount of water that can be incorporated into the perfume/glycol ether mixtures, before phase separation.

| GLYCOL ETHER | % PERFUME IN MIXTURE | | | | |
| --- | --- | --- | --- | --- | --- |
| | 10 | 20 | 30 | 40 | 50 |
| PGMBE | 10 | — | — | — | — |
| DEGMEE | 15 | 10 | 10 | 10 | — |
| DEGDME | 20 | 10 | — | — | — |
| TPGMME | 20 | 10 | 10 | — | — |
| PGMPE | 20 | 10 | 10 | — | — |
| PGMME | 20 | 10 | 10 | 10 | — |
| DPGMME | 20 | 20 | 10 | 10 | — |
| PGMEE | 30 | 20 | 10 | 10 | — |
| DEGMBE | 60 | 40 | 20 | 20 | 10 |

As can be seen from the table DEGMBE can tolerate a far larger amount of water at a specified perfume concentration than any of the other glycol ethers."

For the purposes of the foregoing table and for use throughout the instant application, the following terms are defined:

DEGMEE: the compound having the structure:

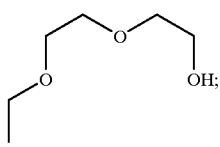

DEGDME: the compound having the structure:

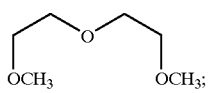

TPGMME: the compound having the structure:

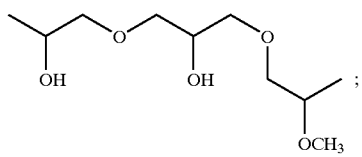

PGMPE: the compound having the structure:

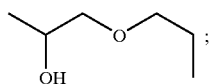

PGMME: the compound having the structure:

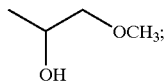

DPGMME: the compound having the structure:

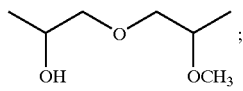

PGMBE: the compound having the structure:

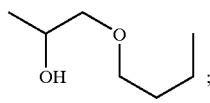

DEGMBE: the compound having the structure:

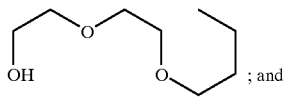; and

PGMEE: the compound having the structure:

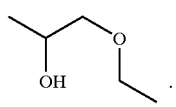.

It is set forth at column 4, lines 15–17 of U.S. Pat. No. 4,663,081:

"As can be seen from the table DEGMBE can tolerate a far larger amount of water at a specified perfume concentration than any of the other glycol ethers."

In view of toxicity problems associated with DEGMBE having the structure:

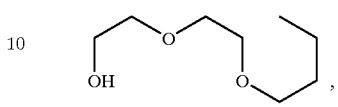

it has become apparent that a substitute for the system set forth in U.S. Pat. No. 4,663,081 is needed.

It is an object of our invention to provide such substitution means.

PCT Application No. 97/45516 published on Dec. 4, 1997 discloses and claims a phase-stable liquid refreshment and cleaning composition comprising:

(a) butoxy propoxy propanol; or other alkoxylated alkoxy propanol solvent (defined according to one of the structures:

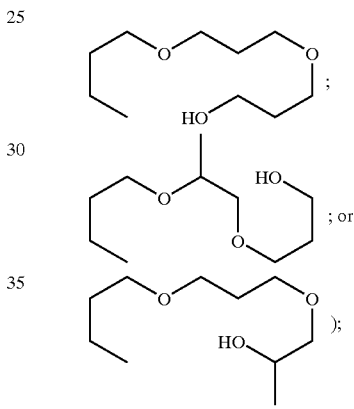

(b) water;
(c) optionally, a minor amount of nonionic surfactant; and
(d) an effective, phase stabilizing amount of a member selected from the group consisting of alkyl sulfate surfactant, alkyl ethoxy sulfate surfactant and mixtures thereof.

However, the PCT Application No. 97/45516 does not teach the problems solved by our invention.

THE INVENTION

Our invention is directed to a single phase aqueous surface-active agent-free air freshening composition characterized in that it is (a) nontoxic; (b) nonmutagenic; and (c) environmentally friendly, consisting essentially of:

(i) 30–70 weight percent water;
(ii) 5–20 weight percent of a fragrance composition wherein at least 60% of its composition consists of one or more substances having a C $\log_{10} P \leq 2.5$ and no more than 40% of any of the components of the perfume composition has a C $\log_{10} P$ in the range of $2.5 < C \log_{10} P \leq 7.5$; and
(iii) 30–60 weight percent of a mixture of two glycol ether compounds, one of which is dipropylene glycol monomethyl ether having the structure:

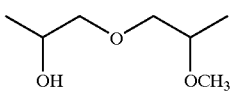

and the other of which is a compound defined according to the structure:

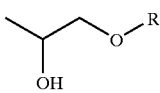

wherein R is n-propyl or n-butyl. As is evident from reading the specification, any shortfall of ingredients as set forth by the percentages herein are readily made up by the addition of water, i.e., Qs to 100%.

A second embodiment of the invention provides a stain removal wipe with the components set forth hereinabove. More specifically, the wipes contain a mixture of (i) dipropylene glycol methyl ether and (ii) propylene glycol propyl ether or propylene glycol butyl ether in an aqueous solution. Fragrance is also included at a level of from about 0.01 to about 10 weight percent of the total solution weight, preferably from about 0.05 to about 8 and most preferably from about 0.1 to about 5 weight percent.

Optionally, a preservative is included in the aqueous solution. The total level of preservative is less than or equal to 1 weight percent of the aqueous solution. Suitable preservatives include, but are not limited to, methyl/ethyl/propyl/butyl paraben, EUXYL® K400, trademark of Schulke & Mayr GmbH of the Federal Republic of Germany and GERMALL® 11, trademark of ISP Chemicals Inc. of Chatham, N.J.

Also optionally included in the solution are chelators at a level of from about 0.01 to about 0.3 weight percent, preferably from about 0.05 to about 0.25 and most preferably at a level of about 0.2 weight percent. Suitable chelators include EDTA, and DEQUEST® phosphonate, trademark of Solutia Inc. of St. Louis, Mo.

The wipes of the present invention contain little or no surfactant or emulsifier materials. The wipes will contain less than 0.1 weight percent surfactant or emulsifier, preferably less than 0.05 weight percent of the aqueous solution and in a most preferred embodiment, no surfactant or emulsifier will be present.

The advantage of the wipes of the present invention is that the highly aqueous, low solvent, little or no surfactant system of the present invention is that it is capable of retaining the fragrance in solution. A further advantage of the wipes is the lack of residue after use and yet the wipe still has good performance and fragrance.

The wipe itself is preferably made of a non-woven material made from polyethylene, polypropylene, polyesters including polyester terphthalate and blends and copolymers of these materials. The wipe typically contains up to about 10 weight percent aqueous solution as described hereinabove, preferably from about 0.1 to about 8 and most preferably from about 1 to about 5 weight percent solutions.

The n-octanol/water partitioning coefficient of a perfume material indicated by the term "P" is the ratio between its equilibrium concentrations in n-octanol and in water. The perfume materials used in our invention have an n-octanol/water partitioning coefficient "P" of between about 1 and about $10^{7.5}$ with at least 60% of the perfume components having a partitioning coefficient of between about 1 and about $10^{2.5}$. Since the partitioning coefficients of the perfume compositions of this invention have values of between about 1 and about $10^{7.5}$, they are more conveniently given in the form of their logarithm to the base 10, $\log_{10}$ P. Thus, the perfume materials useful in the practice of our invention have a $\log_{10}$ P of between about 1 and about 7.5 as indicated, supra, wherein 60% of the components of the perfume composition have a $\log_{10}$ P of between about 1 and about 2.5 as indicated, supra.

The $\log_{10}$ P of many perfume ingredients have been reported; for example, the Pomona 92 database, available from Daylight Chemical Information Systems, Inc. (Daylight CIS), Irvine, Calif., contains many, along with citations to the original literature. However, the $\log_{10}$ P values are most conveniently calculated by the "CLOGP" program, also available from Daylight CIS. This program also lists experimental $\log_{10}$ P, values when they are available in the Pomona 92 database. The "calculated $\log_{10}$ P" is determined by the fragment approach of Hansch and Leo (*Comprehensive Medicinal Chemistry*, Volume 4, C. Hansch, P. G. Sammens, J. B. Taylor and C. A. Ramsden, Editors, page 295, Pergamon Press, 1990, incorporated by reference herein). The fragment approach is based on the chemical structure of each component of the perfume material and takes into account the numbers and types of atoms, the atom connectivity and chemical bonding. The calculated $\log_{10}$ P values, which are the most reliable and widely used estimates for this physicochemical property, are preferably used instead of the experimental $\log_{10}$ P values in the selection of perfume materials useful in the practice of our invention.

More specifically, the perfume materials useful in the practice of our invention having a C $\log_{10}$ P$\leq$2.5 are as follows:

| Perfume Ingredients | Approximate Boiling Point | C $\log_{10}$P |
|---|---|---|
| Benzaldehyde | 179 | 1.480 |
| Benzyl acetate | 215 | 1.960 |
| l-Carvone | 231 | 2.083 |
| Hydroxycitronellal | 241 | 1.541 |
| Linalool | 198 | 2.429 |
| Phenyl ethyl alcohol | 220 | 1.183 |
| Coumarin | 291 | 1.412 |
| Eugenol | 253 | 2.307 |
| Indole | — | 2.142 |
| Methyl dihydrojasmonate | 310 | 2.275 |
| β-Methyl naphthyl ketone | 300 | 2.275 |
| Vanillin | 285 | 1.580 |

For the purposes of our invention, the compounds defined according to the structure:

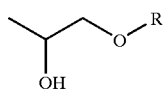

wherein R is n-propyl or n-butyl, are shown by the symbol: [P$_n$R].

The range of weight ratios of the dipropylene glycol monomethyl ether having the structure:

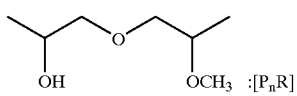 :[P$_n$R]

varies from about 1:1 up to about 5:1.

The following example illustrates the invention, but the invention is only limited by the claims.

EXAMPLE I

The following fragrance is prepared:

| Ingredients | Parts by Weight | C log$_{10}$P |
|---|---|---|
| Benzaldehyde | 20 | 1.48 |
| Benzyl acetate | 20 | 1.960 |
| l-Carvone | 20 | 2.083 |
| Hydroxycitronellal | 20 | 1.541 |
| Linalool | 20 | 2.429 |
| Phenyl ethyl alcohol | 20 | 1.183 |
| Coumarin | 20 | 1.412 |
| Eugenol | 20 | 2.307 |
| Indole | 5 | 2.142 |
| Methyi dihydrojasmonate | 10 | 2.275 |
| β-Methyl naphthyl ketone | 20 | 2.275 |
| Vanillin | 35 | 1.580 |
| Phenyl heptanol | 20 | 3.478 |
| δ-Undecalactone | 20 | 3.830 |
| Patchouli alcohol | 20 | 4.530 |
| Linalyl benzoate | 20 | 5.233 |

At the level of 10%, the resulting fragrance is admixed with the following materials:

EXAMPLE I(A)

(a) 15 parts by weight of propylene glycol butyl ether having the structure:

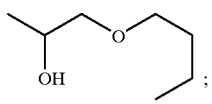 ;

(b) 37.5 parts by weight of dipropylene glycol methyl ether having the structure:

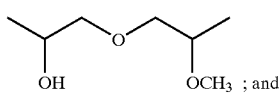 ; and (c) 37.5 parts by weight of water
thereby forming a clear, single phase mixture.

EXAMPLE I(B)

(a) 10 parts by weight of propylene glycol butyl ether;
(b) 30 parts by weight of dipropylene glycol methyl ether; and
(c) 50 parts by weight of water
thereby forming a clear, single phase mixture.

EXAMPLE I(C)

(a) 12.5 parts by weight of propylene glycol butyl ether;
(b) 35 parts by weight of dipropylene glycol methyl ether; and
(c) 42.5 parts by weight of water
thereby forming a clear, single phase mixture.

EXAMPLE I(D)

(a) 10 parts by weight of propylene glycol butyl ether;
(b) 35 parts by weight of dipropylene glycol methyl ether; and
(c) 45 parts by weight of water
thereby forming a clear, single phase mixture;

EXAMPLE I(E)

(a) 10 parts by weight of propylene glycol butyl ether;
(b) 45 parts by weight of dipropylene glycol methyl ether; and
(c) 35 parts: by weight of water
thereby forming a clear, single phase mixture.

EXAMPLE I(F)

(a) 5 parts by weight of propylene glycol butyl ether;
(b) 42.5 parts by weight of dipropylene glycol methyl ether; and
(c) 32.5 parts by weight of water
thereby forming a clear, single phase mixture.

EXAMPLE I(G)

(a) 10 parts by weight of propylene glycol butyl ether;
(b) 30 parts by weight of dipropylene glycol methyl ether; and
(c) 50 parts by weight of water
thereby forming a clear, single phase mixture.

EXAMPLE I(H)

(a) 15 parts by weight of propylene glycol butyl ether;
(b) 10 parts by weight of dipropylene glycol propyl ether having the structure:

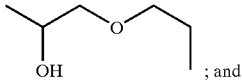 ; and (c) 65 parts by weight of water
thereby forming a clear, single phase mixture.

EXAMPLE I(I)

(a) 25 parts by weight of propylene glycol methyl ether;
(b) 20 parts by weight of dipropylene, glycol n-propyl ether; and
(c) 45 parts by weight of water
thereby forming a clear, single phase mixture.

EXAMPLE I(J)

(a) 20 parts by weight of propylene glycol methyl ether;
(b) 15 parts by weight of dipropylene glycol n-propyl ether; and
(c) 55 parts by weight of water
thereby forming a clear, single phase mixture.

EXAMPLE I(K)

(a) 10 parts by weight of propylene glycol n-butyl ether;
(b) 35 parts by weight of dipropylene glycol methyl ether; and
(c) 45 parts by weight of water thereby forming a clear, single phase mixture.

EXAMPLE I(L)

(a) 10 parts by weight of propylene glycol n-butyl ether;
(b) 40 parts by weight of dipropylene glycol methyl ether; and
(c) 40 parts by weight of water thereby forming a clear, single phase mixture.

EXAMPLE I(M)

(a) 10 parts by weight of propylene glycol butyl ether;
(b) 40 parts by weight of dipropylene glycol methyl ether; and
(c) 40 parts by weight of water thereby forming a clear, single phase mixture.

EXAMPLE I(N)

(a) 10 parts by weight of propylene glycol butyl ether;
(b) 35 parts by weight of dipropylene glycol methyl ether; and
(c) 45 parts by weight of water thereby forming a clear, single phase mixture.

EXAMPLE I(O)

(a) 17.5 parts by weight of propylene glycol butyl ether;
(b) 37.5 parts by weight of dipropylene glycol methyl ether; and
(c) 35 parts by weight of water thereby forming a clear, single phase mixture.

Each of the foregoing: mixtures of Examples I(A)–I(O) is separately admixed with the following ingredients:

| Ingredient | Weight Percent |
| --- | --- |
| UVASORB ® | 0.002 |
| KATHON ® CG | 0.05 |
| dye | 0.05 |

Each of the resulting mixtures is used in an IFF prototype non-electric wick air freshener. In all cases, at steady state, the period of exhaustion of the wick was greater than 45 days. The following table sets forth the periods of exhaustion and perfume emanated as a percent of original for each example:

| Example | Exhaustion Days | Perfume Emanated (% of original) |
| --- | --- | --- |
| I(A) | 62 | 68 |
| I(B) | 57 | 72 |
| I(C) | 71 | 82 |
| I(D) | 58 | 84 |
| I(E) | 69 | 78 |
| I(F) | 82 | 89 |

-continued

| Example | Exhaustion Days | Perfume Emanated (% of original) |
| --- | --- | --- |
| I(G) | 74 | 73 |
| I(H) | 67 | 69 |
| I(I) | 64 | 80 |
| I(J) | 74 | 82 |
| I(K) | 73 | 79 |
| I(L) | 82 | 90 |
| I(M) | 84 | 89 |
| I(N) | 71 | 78 |
| I(O) | 74 | 77 |

In general, the systems of our invention show a vast improvement over the systems of the prior art; with the additional features that the systems of our invention are nontoxic, nonmutagenic and are environmentally friendly.

The air freshener devices that may be used in the instant case are those devices set forth in U.S. Pat. No. 4,663,081 issued on May 5, 1987, the specification for which is incorporated by reference herein.

EXAMPLE II

The fragrance of Example 1 is used in the following formulation:

| Ingredient | Weight Percent |
| --- | --- |
| Fragrance | 0.2 weight percent |
| Preservative (Germall 115) | 0.1 weight percent |
| Dipropylene glycol monomethyl ether | 1.25 weight percent |
| Propylene glycol propyl ether | 1.25 weight percent |
| Water | to 100 weight percent |

The above formulation is applied to a non-woven wipe comprised of a blend of polypropylene and polyethylene. The wipe contains approximately 2.7 weight percent of the above formulation. The wipe is useful in removing stains from clothing as well as hard surfaces.

What is claimed is:

1. A wipe having <0.1 weight percent surfactant or emulsifier contained therein and consisting essentially of a non-woven wipe base having applied thereto up to about 10 weight percent of a single phase, aqueous, substantially surface active agent-free solution characterized in that the solution is (a) non-toxic, (b) non-mutagenic and (c) environmentally friendly comprising:

i. 0.01–10 weight percent of a fragrance composition wherein at least 60% of its composition consists of one or more substances having a C $\log_{10} P \leq 2.5$ and no more than 40% of any of the components of the perfume composition has a C $\log_{10} P$ in the range of $2.5 < C \log_{10} P < 7.5$;

ii. a mixture of two glycol ether compounds, one of which is the 1,2-dipropylene glycol monomethyl ether having the structure:

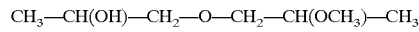

$CH_3$—$CH(OH)$—$CH_2$—$O$—$CH_2$—$CH(OCH_3)$—$CH_3$ and the other of which is a 1,2-propylene glycol ether defined according to the: structure:

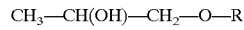

$CH_3$—$CH(OH)$—$CH_2$—$O$—$R$ wherein R is selected from the group consisting of n-propyl and n-butyl and wherein the range of weight ratios of 1,2-dipropylene glycol monomethyl ether: 1,2-propylene glycol ether is from about 1:1 up to about 5:1; and iii. the remainder, water.

2. The wipe of claim 1 wherein R is n-propyl.

3. The wipe of claim 1 wherein R is n-butyl.

4. The wipe of claim 1 wherein the weight ratio of 1,2-dipropyleneglycol monomethyl ether: 1,2-propylene glycol ether is about 1:1.

5. The wipe of claim 1 wherein the weight percent of fragrance composition is from about 0.05 up to about 8 weight percent.

6. The wipe of claim 1 wherein the weight percent of fragrance composition is from about 0.1 up to about 5 weight percent.

7. The wipe of claim 1 wherein the level of preservative is $\leq 1$ weight percent of the aqueous solution.

8. The wipe of claim 1 wherein the non-woven wipe base is a material selected from the group consisting of polyethylene, polypropylene, polyester, a blend thereof and a copolymer thereof.

9. The wipe of claim 1 containing from about 0.1 up to about 8 weight percent of single phase, aqueous, substantially surface active agent-free solution.

10. The wipe of claim 1 containing from about 1 up to about 5 weight percent of single phase, aqueous, substantially surface active agent-free solution.

11. The wipe of claim 1 containing 2.5 weight percent of said mixture of two glycol ether compounds.

12. The wipe of claim 1 containing 2.5 weight percent of said mixture of two glycol ether compounds.

* * * * *